United States Patent [19]
Gerry et al.

[11] Patent Number: 5,447,514
[45] Date of Patent: Sep. 5, 1995

[54] CIRCULAR ANASTOMOSIS DEVICE

[75] Inventors: Stephen W. Gerry, Bethel; Philip D. Calabrese, Danbury; Timothy O. Van Leeuwen, Brookfield, all of Conn.

[73] Assignee: United States Surgical Corporation, Norwalk, Conn.

[21] Appl. No.: 130,224

[22] Filed: Oct. 1, 1993

[51] Int. Cl.⁶ ............................................. A61B 17/00
[52] U.S. Cl. ..................... 606/153; 606/151; 227/175; 227/178; 227/179
[58] Field of Search ............... 606/142, 143, 151, 153, 606/213, 215; 227/175–181, 19, 901; 604/167

[56] References Cited

U.S. PATENT DOCUMENTS

| | | |
|---|---|---|
| 4,027,510 | 6/1977 | Hiltebrandt . |
| 4,316,624 | 2/1982 | Davlin ............................ 285/158 |
| 4,485,817 | 12/1984 | Swiggett ........................ 227/179 |
| 4,488,523 | 12/1984 | Shichman ...................... 227/180 |
| 4,576,167 | 3/1986 | Noiles . |
| 4,759,364 | 7/1988 | Boebel ........................... 606/142 |
| 5,005,749 | 4/1991 | Aranyi . |
| 5,009,455 | 4/1991 | Irvine ............................. 285/106 |
| 5,040,715 | 8/1991 | Green et al. . |
| 5,084,057 | 1/1992 | Green et al. . |
| 5,100,420 | 3/1992 | Green et al. . |
| 5,119,983 | 6/1992 | Green et al. . |
| 5,125,553 | 6/1992 | Oddsen et al. . |
| 5,158,222 | 10/1992 | Green et al. . |
| 5,171,249 | 12/1992 | Stefanchik et al. . |
| 5,197,963 | 3/1993 | Parins ............................ 606/46 |
| 5,228,485 | 7/1993 | Lewis et al. ................... 141/83 |
| 5,258,007 | 11/1993 | Spetzler et al. ................ 606/142 |
| 5,333,773 | 8/1994 | Main et al. . |
| 5,364,001 | 11/1994 | Bryan . |
| 5,364,002 | 11/1994 | Green et al. . |

*Primary Examiner*—Stephen C. Pellegrino
*Assistant Examiner*—Jeffrey A. Schmidt

[57] ABSTRACT

A surgical instrument for performing a circular anastomosis is disclosed. The instrument is provided with sealing means to permit use during endoscopic procedures. The sealing means includes a first, O-ring seal disposed intermediate of a compression member, wherein the first seal is configured and dimensioned to at least partially contact an outer portion of the compression member and an inner portion of an outer tube. The second seal at least partially disposed proximal the first seal and has a first diameter portion, a second diameter portion and is disposed about the compression member. The compression member has at least one aperture which the second seal is adapted to engage.

6 Claims, 3 Drawing Sheets

CIRCULAR ANASTOMOSIS DEVICE

BACKGROUND OF THE INVENTION

1. Field of the Invention

The present invention relates to surgical instruments for applying surgical staples to body tissue, and more particularly to a sealed apparatus for applying an annular array of surgical staples.

2. Discussion of the Related Art

Surgical stapling devices for applying an annular array of staples to tissue are well known in the art. These devices typically include a stapling assembly and an anvil member at the distal end of the apparatus. The stapling assembly generally includes a circular array of staples and means for expelling the staples against the anvil member. The anvil member typically includes means for completing the circular anastomosis, i.e. an array of bucket-shaped members against which clinch the staples are formed after being expelled from the stapling assembly.

Surgical stapling devices for applying an annular array of staples are well known in gastric and esophageal surgery, for example, in classic or modified gastric reconstruction typically formed in an end, to-end, end-to-side or side-to-side manner. One such instrument is the Premium CEEA® surgical stapler, manufactured and sold by United States Surgical Corporation. In use, the instrument typically is positioned within the lumen of an organ such as the stomach, esophagus or intestine in order to perform the anastomosis. The tissue is positioned between the anvil and the stapling assembly and is typically tied off, for example, by a purse string suture. Thereafter, the anvil member is advanced toward the stapling assembly by rotation of a rotatable knob or wing nut assembly at the proximal end of the instrument. When proper approximation is achieved, the staples are expelled from the fastener assembly. A circular knife typically follows the application of the staples to excise unwanted tissue at the anastomosis site. The instrument is then removed from the lumen of the organ.

To a large degree, the recent explosion in laparoscopic surgical procedures may be attributed to the development of mechanical devices particularly adapted for use in a laparoscopic environment. For example, U.S. Pat. Nos. 5,084,057 and 5,100,520 to Green, et al. describe an endoscopic multiple clip applier which enabled the surgical community to fully realize the potential of endoscopic cholycystectomy. The Green '057 and '420 patents describe, inter alia, a gaseous seal means for obstructing the passage of gas from the insufflated body cavity.

Providing a sealing system for a circular anstomosis instrument is recognized in the art. The present invention provides a uniquely structured sealing system which not only effectively seals the instrument but is easy to manufacture and assemble and does not significantly increase the cost of the instrument.

SUMMARY OF THE INVENTION

The present invention provides a circular anastomosis instrument having means for preventing the flow of gas through the instrument during surgical procedures. Two seals are positioned within the body of the instrument to prevent/inhibit flow of gases through the instrument. The first seal is an O-ring positioned between an inner staple firing/compression member and the outer tube of the instrument. The second seal is at least partially positioned proximal the first seal, is positioned about a portion of the anvil approximation mechanism of the instrument and protrudes through apertures in a compression member. The two seals, in combination, permit surgeons to perform a circular anastomosis while the patient's body is at least partially insufflated.

BRIEF DESCRIPTION OF THE DRAWINGS

The foregoing features of the present invention will become more readily apparent and may be understood by referring to the following detailed description of an illustrative embodiment of the surgical stapling apparatus and its novel sealing system, taking in conjunction with the accompanying drawings, in which.

DETAILED DESCRIPTION OF THE INVENTION

Figure 1:
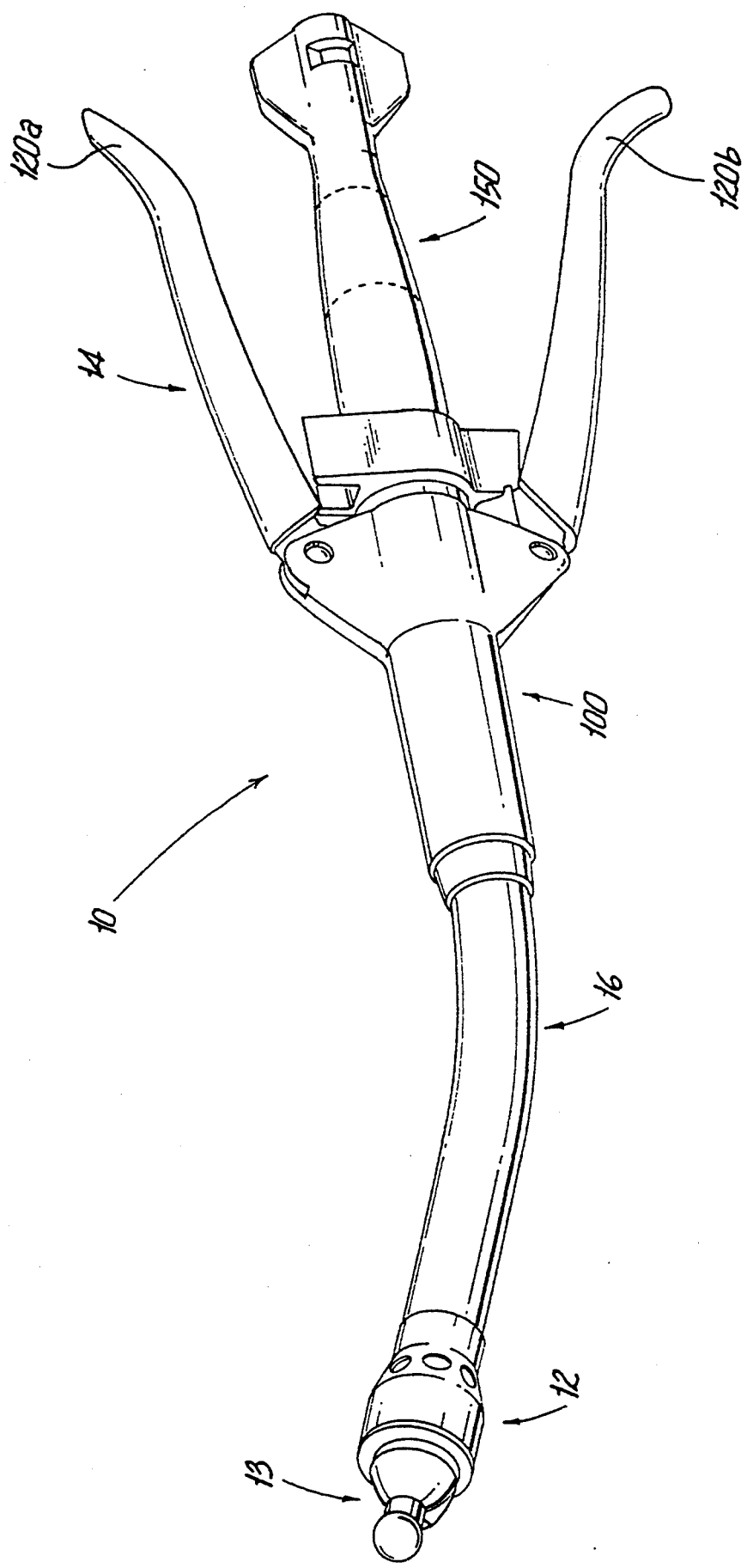
FIG. 1 is a perspective view of a surgical stapler incorporating a sealing system of the present invention.

An illustrative embodiment of a circular anastomosis surgical stapler 10 shown generally in FIG. 1. A typical application of stapler 10 is connecting together two sections of hollow tubular body organ, (e.g., two intestinal sections) by means of an annular array of staples which surrounds a lumen or passageway between the interiors of the connected organ sections. Stapler 10 includes distal stapling assembly 12, anvil member 13, proximal actuator assembly 14 and longitudinal shaft assembly 16 for connecting distal and proximal assemblies and for transmitting actuation forces and motions from the actuator assembly to the stapling assembly. Shaft assembly 16 can be straight or have a longitudinally curved portion as shown. In the particular embodiment shown in the drawing, this curved portion is an arc of a circle and therefore has a generally uniform radius along its length. Detailed descriptions and methods of using similar circular anastomosis devices are disclosed, for example, in commonly assigned U.S. Pat. Nos. 4,576,167, 5,005,749 and 5,119,983, which are incorporated herein by reference. Surgical stapler 10 can also be adapted to apply anastomosis rings and the like.

Figure 2:
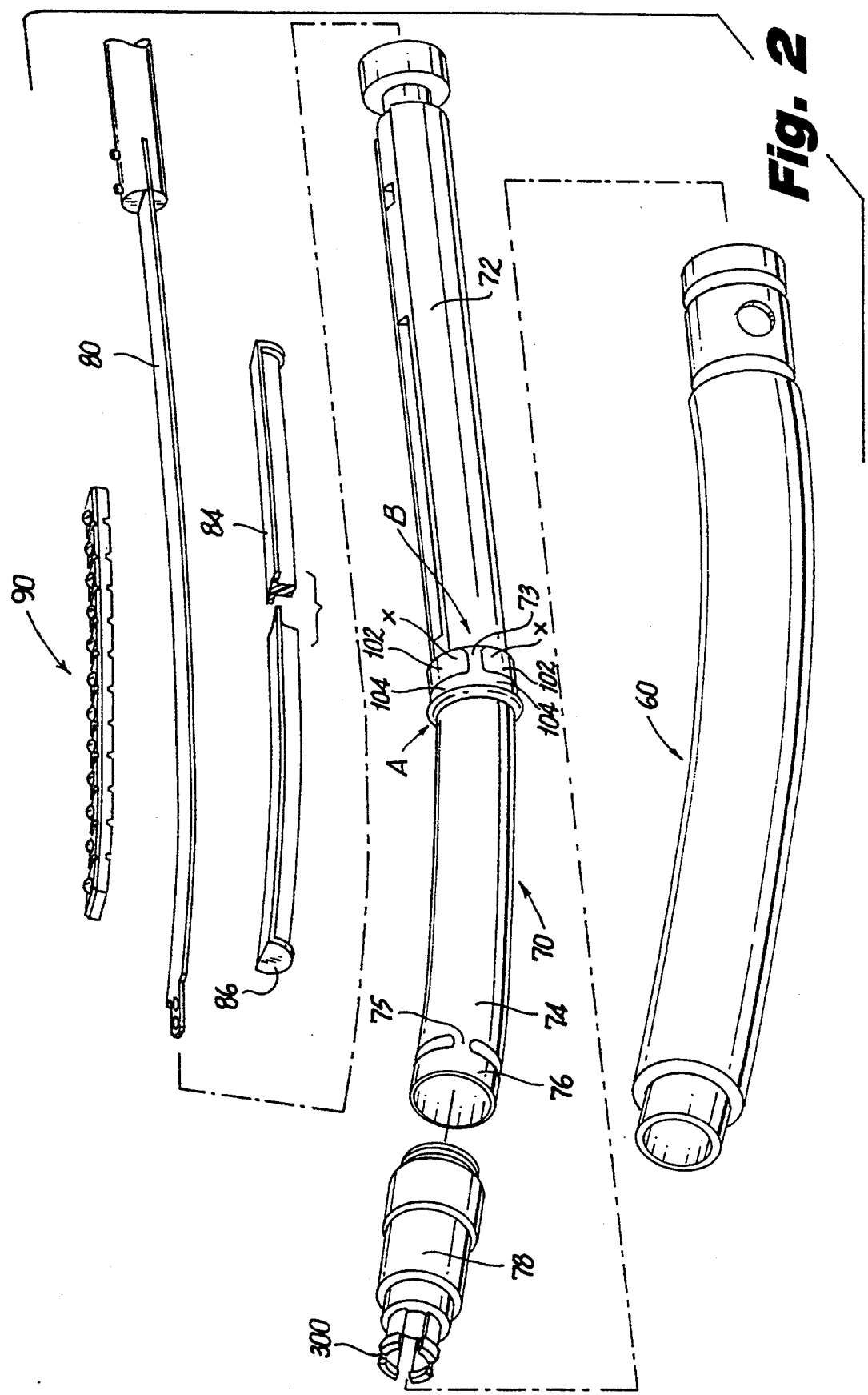
FIG. 2 illustrates an exploded perspective view of a portion of the apparatus of FIG. 1, showing the sealing system of the present invention.

With reference to FIGS. 1 and 2, the proximal end of outer shaft tube 60 is secured to housing 100. Inner tube 70 is disposed within outer shaft tube 60 and is mounted for longitudinal motion relative to tube 60. The distal end of inner tube 70 is threadably connected to extension tube 78 which is also longitudinally movable within outer tube 60. Tubes 70 and 78 constitute a compression member for transmitting a longitudinal compression force produced by operation of handles 120a and 120b of actuator assembly 14 and serve to transmit forces to stapling assembly 12. By squeezing handles 120a and 120b towards each other, tubes 70 and 78 are caused to move distally, thereby causing the ejection of staples, as is known in the art and described in detail in the above commonly assigned patents.

Tube 70 has a straight proximal portion 72, a curved intermediate portion 74, and distal portion 76. Notched sections 73 and 75 separate sections 72 and 74, and 74 and 76 respectively. Apertures X, adjacent sections 74, 75 and 76, allow some bending, thereby providing flexibility in tube 70. The material in sections 73 and 75 can be selected to yield when tube 70 is bent or flexed. The distal end of extension tube 78 includes quills 300 which extend into staple assembly 12 where the quills serve to contact staple pushers (not shown).

Turning the sealing system of the present invention, with reference to FIG. 2, two seals are provided. The first seal A is an O-ring and located distal of section 73. O-ring A can be manufactured from any material suitable for providing a gas seal such as butyl rubber. Tube portion 74 can have a circumferential groove to facilitate placement and securement of seal A thereto.

Figure 3:
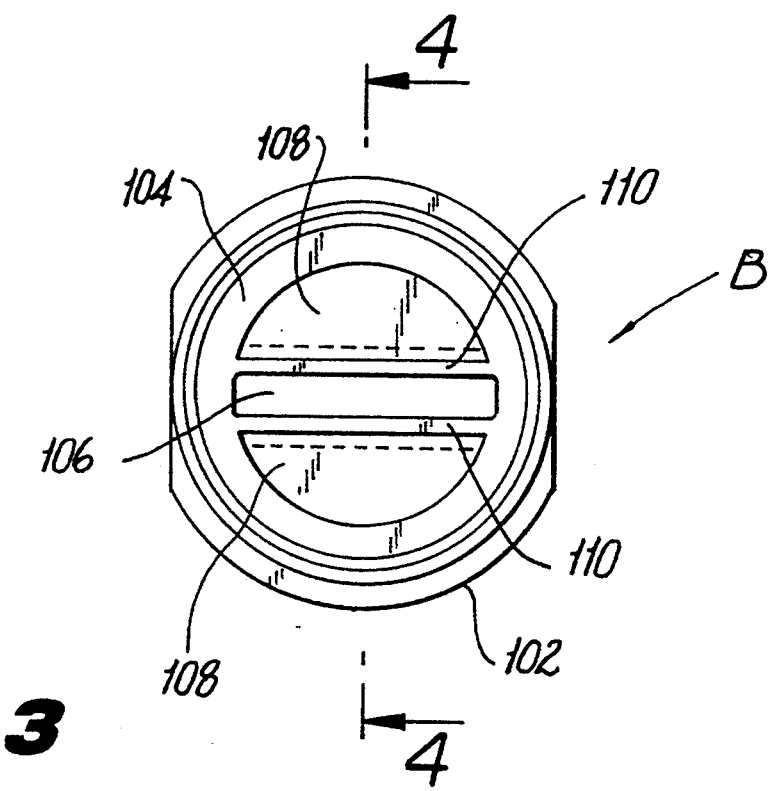
FIG. 3 illustrates a top view of the proximal end of one the seals of the present invention.
Figure 4:
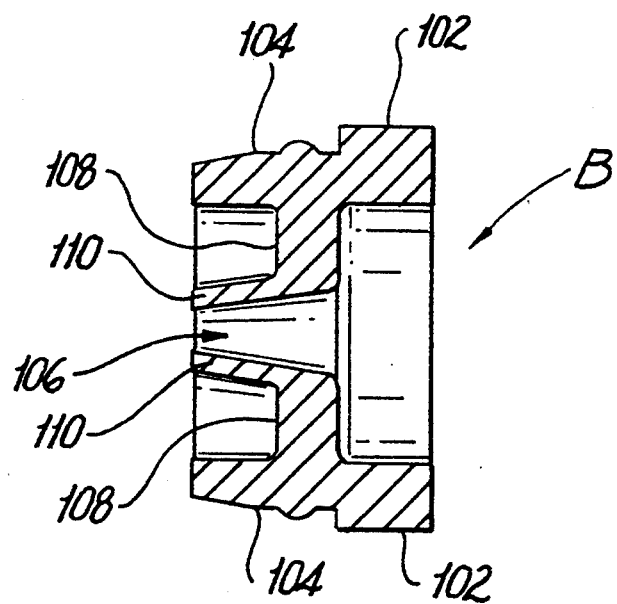
FIG. 4 illustrates a side elevational view along the lines 4—4 of the seal of FIG. 3.

The second seal B is located in the distal end of proximal portion 72 of tube 70. With reference to FIGS. 2-4, seal B has a first, large diameter portion 102 which is configured and dimensioned to partially fit in apertures X of section 73 and a second, narrow diameter portion 104 which extends distally and contacts the inner surface of tube 70. Seal B further comprises longitudinal recessed aperture 106, defined by shoulders 108 and inwardly projecting walls 110, which permit band(s) 80 to pass therethrough. Preferably, several bands 80 may be used in a stacked relationship, each passing through seal B at aperture 106. Seal B is preferably manufactured from silicone rubber.

In operation, seal A prevents gas from flowing between inner compression tube 70 and outer tube 60. Seal B prevents gas from flowing through both apertures X in section 73 and through the inside of tube 70.

It will be understood that the foregoing is only illustrative of the principles of the inventions and that various modifications can be made by those skilled in the art without departing from the scope and spirit of the invention.

What is claimed is:

1. A surgical instrument for performing a circular anastomosis comprising:

a shaft assembly having an inner compression member and an outer tube with proximal and distal end portions, the compression member having two apertures at an intermediate portion thereof;

a fastener assembly disposed at said outer tube distal end portion;

a housing portion disposed at said outer tube proximal end portion;

an anvil assembly disposed distal of said fastener assembly and means for manipulating said anvil assembly disposed proximal of housing portion, wherein at least one elongate member is disposed within said shaft assembly, said elongate member transferring movement from said anvil manipulating means to said anvil;

an actuator assembly associated with said housing portion for manipulating said inner compression member; and sealing means positioned within said shaft assembly for inhibiting the flow of gases therethrough, said sealing means comprising a first, O-ring seal disposed intermediate of said compression member, said first seal configured and dimensioned to at least partially contact an outer portion of said compression member and an inner portion of said outer tube, and a second seal at least partially disposed proximal said first seal, said second seal having a first diameter portion and a second, smaller diameter portion extending distally from said first diameter portion, the second diameter portion being entirely disposed within said compression member and the first diameter portion being at least partially disposed within said two compression member apertures.

2. The surgical instrument of claim 1, wherein said compression member is tubular in configuration.

3. The surgical instrument of claim 2, wherein said tubular compression member has a circumferential grove on an outer surface thereof and said first seal is at least partially disposed within said groove.

4. The surgical instrument of claim 1, wherein said first seal is at least partially fabricated from butyl rubber.

5. The surgical instrument of claim 1, wherein said second seal is at least partially fabricated from silicone rubber.

6. The surgical instrument of claim 1, wherein said second seal has a longitudinal aperture defined by a pair of shoulders extending radially inward from an inner surface of the seal and by a pair of walls extending longitudinally from the shoulders.

* * * * *